(12) United States Patent
Goble (10) Patent No.: US 10,660,558 B2
(45) Date of Patent: May 26, 2020

(54) APPARATUS AND METHOD FOR DETECTING CLINICALLY RELEVANT CHANGES IN BALANCE

(71) Applicant: SAN DIEGO STATE UNIVERSITY RESEARCH FOUNDATION, San Diego, CA (US)

(72) Inventor: Daniel J. Goble, San Diego, CA (US)

(73) Assignee: SAN DIEGO STATE UNIVERSITY RESEARCH FOUNDATION, San Diego, CA (US)

( * ) Notice: Subject to any disclaimer, the term of this patent is extended or adjusted under 35 U.S.C. 154(b) by 99 days.

(21) Appl. No.: 14/779,398

(22) PCT Filed: Feb. 28, 2014

(86) PCT No.: PCT/US2014/019331
§ 371 (c)(1),
(2) Date: Sep. 23, 2015

(87) PCT Pub. No.: WO2014/158698
PCT Pub. Date: Oct. 2, 2014

(65) Prior Publication Data
US 2016/0058357 A1 Mar. 3, 2016

Related U.S. Application Data

(60) Provisional application No. 61/806,738, filed on Mar. 29, 2013.

(51) Int. Cl.
*A61B 5/00* (2006.01)
*A61B 5/103* (2006.01)
*A61B 5/11* (2006.01)

(52) U.S. Cl.
CPC .......... *A61B 5/4023* (2013.01); *A61B 5/1036* (2013.01); *A61B 5/1038* (2013.01); *A61B 5/112* (2013.01)

(58) Field of Classification Search
CPC ...... A61B 5/4023; A61B 5/1036–1038; A61B 5/112; G01G 19/44
See application file for complete search history.

(56) References Cited

U.S. PATENT DOCUMENTS 3,027,761 A * 4/1962 Lauro .................. A61B 5/1036
177/245
5,388,591 A * 2/1995 De Luca .............. A61B 5/1036
600/592

(Continued)

FOREIGN PATENT DOCUMENTS

EP 1074217 A1 2/2001

OTHER PUBLICATIONS

International Search Report issued in corresponding PCT Application No. PCT/US2014/019331, dated May 27, 2014.

*Primary Examiner* — Sean P Dougherty
*Assistant Examiner* — David Joseph Fernandez-Fidalgo
(74) *Attorney, Agent, or Firm* — Juneau & Mitchell IP Law Firm; Todd L. Juneau (57) ABSTRACT

Systems and methods facilitating objective evaluations of subjects to facilitate detecting clinically relevant changes in balance are provided. The system includes a portable balance board with a sensor in each of four feet for detecting downward force. Each sensor is communicatively coupled to a circuit board with a wired or wireless communication capability. A subject stands on the balance board and each sensor sends a signal to the circuit board, which communicates the four signals to a companion device that uses the signals to calculate the center of pressure ("COP") of the subject over time. The subject can perform the BESS test and the resulting COP data is used to calculate a field path length for the subject. The field path length is compared to a previously determined baseline path length for the subject (Continued)

to detect any clinically relevant change in balance of the subject.

1 Claim, 6 Drawing Sheets

(56) References Cited

U.S. PATENT DOCUMENTS

| | | | |
|---|---|---|---|
| 6,389,883 B1 | 5/2002 | Berme et al. | |
| 8,764,532 B1* | 7/2014 | Berme | A61B 5/742 434/258 |
| 2002/0011250 A1* | 1/2002 | Stewart | A61B 5/00 128/898 |
| 2003/0010543 A1* | 1/2003 | Montagnino | G01G 19/44 177/177 |
| 2003/0181791 A1* | 9/2003 | Thomas | A61B 5/05 600/300 |
| 2005/0021312 A1* | 1/2005 | Tanaka | A61B 5/103 702/189 |
| 2006/0251334 A1* | 11/2006 | Oba | A61B 5/1122 382/275 |
| 2006/0293613 A1* | 12/2006 | Fatehi | A61B 5/1036 600/587 |
| 2008/0217074 A1* | 9/2008 | Kodaka | G01G 19/44 177/211 |
| 2008/0318703 A1* | 12/2008 | Mooney | A63B 69/3614 473/269 |
| 2009/0062092 A1 | 3/2009 | Mortimer et al. | |
| 2009/0093305 A1* | 4/2009 | Okamoto | A63F 13/10 463/36 |
| 2009/0183928 A1* | 7/2009 | Oseko | G01G 3/1402 177/211 |
| 2010/0023293 A1* | 1/2010 | Walthert | G01G 23/3735 702/101 |
| 2011/0213278 A1* | 9/2011 | Horak | A61B 5/112 600/595 |
| 2012/0253233 A1 | 10/2012 | Greene et al. | |
| 2012/0330178 A1* | 12/2012 | Kraft | A61B 5/6898 600/544 |
| 2014/0081177 A1* | 3/2014 | Eguibar | A61B 5/1036 600/595 |
| 2016/0007902 A1* | 1/2016 | Hewson | A61B 5/11 600/592 |

* cited by examiner

APPARATUS AND METHOD FOR DETECTING CLINICALLY RELEVANT CHANGES IN BALANCE

BACKGROUND

Field of the Invention

The present invention generally relates to detecting clinically relevant changes in balance of a person and more particularly relates to a mobile balance board and method of using the same to detect clinically relevant changes in balance of a person.

Related Art

Conventional methods for evaluating subjects (individual persons) in the field to determine clinically relevant changes in balance are severely limited and suffer from the subjectivity of the human observer. The Balance Error Scoring System ("BESS") is the standard being used in the field today for detecting concussions and the subjective results of BESS tests depend on the training and experience level of the observer. Sports related concussions are a significantly growing public health concern, however post injury evaluation of subjects is severely constrained to the subjective conclusions of human observers of balance tests.

A concussion is a form of mild traumatic brain injury that results in a transient disturbance of brain function due to complex pathophysiological processes. The symptoms associated with concussions vary, but often include loss of consciousness, vertigo, blurred vision and motor disruption. Using the United States as an example, as many as 1.7 million people visit the emergency room each year due to concussive incidents. Further, it has been estimated that concussions represent a 76.5 billion dollar burden to the United States healthcare system at large.

A known contributor to the growing concussion problem is sport-related concussion. Approximately 3.8 million sports-related concussive incidents are reported annually in the United States, accounting for 5-9% of all sports-related injuries. Given these statistics, it is not surprising that those individuals responsible for the care of injured athletes, such as athletic trainers and team physicians, are being increasingly scrutinized for their treatment of this potentially life threatening condition. To this point, one of the greatest challenges identified by sport medicine professionals who treat concussed athletes is a lack of objective/quantifiable information for making decisions regarding when an athlete can safely return to play.

In recent position statements by the American Medical Society and at the 4th International Conference on Concussion in Zurich, balance testing was recognized as an increasingly useful and important aspect in the diagnosis and management of sports-related concussion. Indeed, balance control is a fundamental aspect of many sports activities and reflects an athlete's sensorimotor status by requiring the complex integration of sensory feedback and coordinated motor responses to keep one's center of mass over the body's base of support. Two main approaches have been utilized to assess balance ability in concussed athletes. First, a "high technology" approach has been taken using a scientific grade force plate. Second, "low technology" clinical observation based measures of balance have been implemented that rely on the observational skills of trained professionals to quantify balance ability.

Both approaches to balance assessment have noted strengths and weaknesses. Force plate testing provides a fully objective, valid and reliable means of measuring moments of force to determine balance ability. Force plate testing uses increasingly sophisticated sensors and equipment to measure balance ability and is superior to determinations made by clinical observation based balance tests. However, the use of such sophisticated sensors and equipment to measure moments of force and determine balance ability significantly increases the cost of a scientific grade force plate and $5,000-$20,000 is not feasible for most youth/amateur sports teams. Additionally, force plates typically lack the portability necessary to perform assessments in the field.

Alternatively, clinical observation based balance tests are both portable and very cost effective, requiring no purchase of specialized measurement equipment. The BESS protocol, for example, is the current recommended standard for balance testing in the realm of sports-related concussion. The BESS test involves the performance of six, 20 second balance trials by the athlete that vary in difficulty based on foot stance and support surface (firm vs. foam) conditions. Balance in this test is easily quantified in many environments by having a trained clinician view each balance trial and count the total number of errors observed, such as stepping out of position or moving ones hands from the hips. Unfortunately, evidence regarding the validity/reliability of the BESS has been mixed. In particular, several recent studies show that the BESS is inherently prone to subjectivity and human error.

Therefore, what is needed is a system and method that overcomes these significant problems found in the conventional systems as described above.

SUMMARY

Described herein are solutions to the above described problems that provide objective evaluations of subjects to facilitate detecting clinically relevant changes in balance. In contrast to conventional force plate solutions, the presently described solutions are portable, objective, cost effective, and do not require sophisticated and costly equipment and controlled environmental conditions to accurately measure balance ability. The presently described solutions instead stand in stark contrast to conventional force plate solutions and eliminate the increasingly high cost associated with the increasingly sophisticated equipment required by conventional force plate solutions. The presently described solutions move in an entirely different direction than the conventional force plate solutions by eliminating the increasingly complex moment of force measurements and calculations without loss of accuracy in the measurements of balance ability.

In one embodiment, a portable balance board is provided with sensors in each of four feet and a circuit board and wired or wireless communication capability. A subject stands on the balance board and each sensor sends a signal to the circuit board, which communicates the four signals to a companion processor enabled device that uses the signals to calculate the center of pressure ("COP") of the subject over time. The processor enabled device uses a COP value for each of a plurality of time increments to calculate a field measured path length for the subject and this field measured path length is compared to a previously determined baseline path length for the subject to detect any clinically relevant change in balance of the subject. Alternatively, when no subject specific baseline has been established, the field measured path length can be compared to a previously determined normative path length for a subject having similar demographic characteristics.

In another embodiment, a plurality of balance boards are communicatively coupled to a server device over a data communication network. A variety of subjects are evaluated on each of the balance boards and the raw COP data or calculated path length data is sent to the server along with the associated subject's demographic information. This information is stored on the server and aggregated with other information to provide statistically significant sample data against which future measurements can be evaluated to determine percentile rankings and other normative data.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Certain embodiments disclosed herein provide systems and methods for detecting clinically relevant changes in balance of a person. For example, one method disclosed herein allows for a healthy subject to be evaluated on a mobile balance board prior to an injury event and the objective center of pressure ("COP") data sensed by the balance board is used to establish a baseline path length value for the subject. After an injury event, the subject can be evaluated in the field using the mobile balance board and the resulting field path length value is compared to the baseline path length value to determine whether or not a clinically relevant change in balance of the subject is present. Advantageously, clinically relevant changes in balance of a subject can be used as one factor to objectively determine if the subject has a concussion or other medical condition.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figure 1:
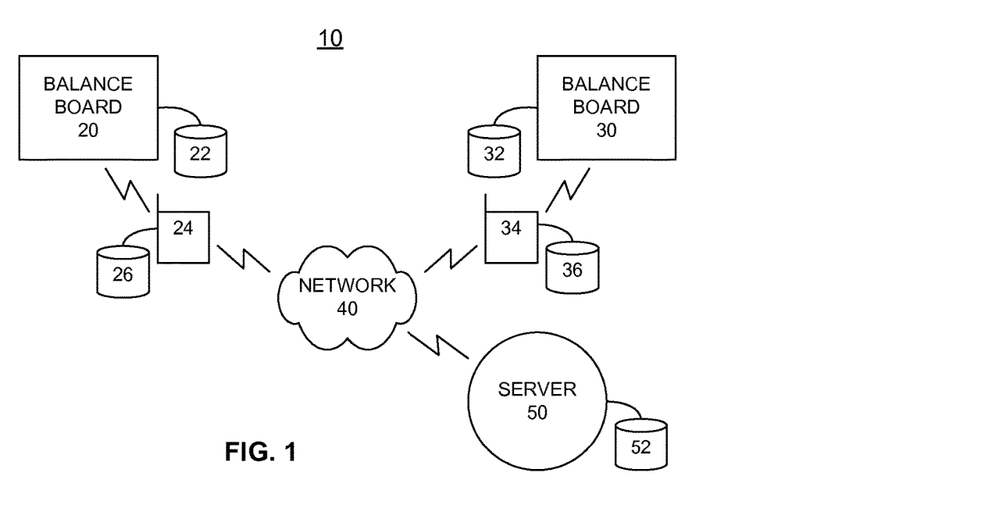
FIG. 1 is a network diagram illustrating an example system for detecting clinically relevant changes in balance of a person according to an embodiment of the invention.

FIG. 1 is a network diagram illustrating an example system 10 for detecting clinically relevant changes in balance of a person according to an embodiment of the invention. In the illustrated embodiment, the system 10 comprises a plurality of balance boards 20 and 30 that are communicatively coupled with processor enabled devices 24 and 34 respectively. The balance board 20 and the processor enabled device 24 may be communicatively coupled wirelessly (e.g., Bluetooth, IrDA, Home RF, SWAP, IEEE 802.11 or the like) or via a wired link (e.g., USB or the like). The balance boards 20 and 30 as well as the processor enabled devices 24 and 34 are each configured with data storage areas, 22, 26, 32 and 36, respectively. In one embodiment, the balance board 20 and the processor enabled device 24 may be integrated into a single apparatus. Similarly, the balance board 30 and the processor enabled device 34 may be integrated into a single apparatus.

The balance boards 20 and 30 and/or the processor enabled devices 24 and 34 can be communicatively coupled with a server 50 via a network 40. The network 40 can be any sort of wired or wireless network, public or private network and may carry data traffic compliant with any of a variety of communication protocols. The network 40 may also be any combination of network and for example may include the combination of networks commonly referred to as the Internet.

The server 50 is configured with a data storage area 52 and is configured to receive data collected from the balance boards 20 and 30 and aggregate the data into one or more collections of population sample data that can be used to compare an individual subject's balance board and demographic data to determine where the individual subject lies within the population sample data as a percentile ranking.

Figure 2A:
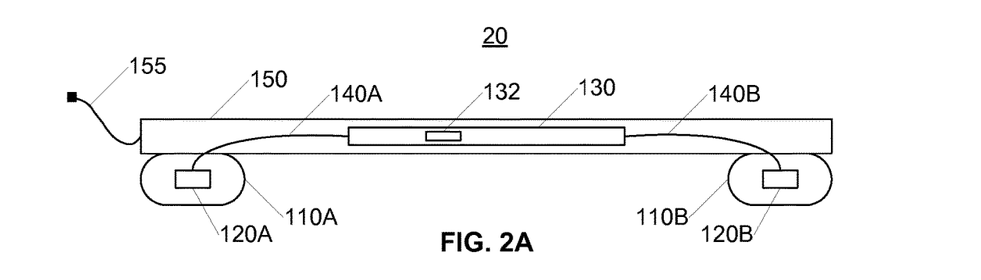
FIG. 2A is a block diagram illustrating a side view of an example balance board according to an embodiment of the invention.

FIG. 2A is a block diagram illustrating an example balance board 20 according to an embodiment of the invention. In the illustrated embodiment, the balance board 20 has a plurality of feet 110A and 110B that are each attached to a platform 150. As shown, the feet 110A and 110B are oriented at the perimeter of the platform 150 to provide optimal stability of the balance board 20 and to provide more accurate COP measurements. In one embodiment, the platform 150 is roughly 20-24 inches in length and 14-15 inches in width and has a thickness sufficient to support up to 500 pounds without adversely affecting data collection by the sensors 120A and 120B that are located in the feet 110A and 110B. The dimensions of the platform 150 are selected such that a subject can stand heel to toe on the platform 150 in the length direction without the subject's heel or the subject's toes extending off of the platform 150. Similarly, the dimensions of the platform 150 are selected such that the subject can stand ankle to ankle on the platform 150 without the outside of the subject's feet extending off of the platform 150.

In one embodiment, the board 20 includes four feet. In alternative embodiments there may be alternative numbers of the plurality of feet. Advantageously, the feet 110A and 110B may be adjustable to accommodate for a sloped or otherwise unlevel surface. Each foot 110A and 110B has a sensor 120A and 120B integrated with the foot. The sensors 120A and 120B are configured to detect a downward force and provide force data to a circuit board 130, for example through communication links 140A and 140B, which can be wired or wireless. In the illustrated embodiment, the circuit board 130 includes a communication module 132 that is configured to send the sensor data to a processor enabled device (not shown) for calculation of COP of a subject standing on the platform. The communication module 132 may send the sensor data to the processor enabled device via a wireless communication link or a wired communication link. For example, USB cable 155 may be employed to send the sensor data to the processor enabled device.

Figure 2B:
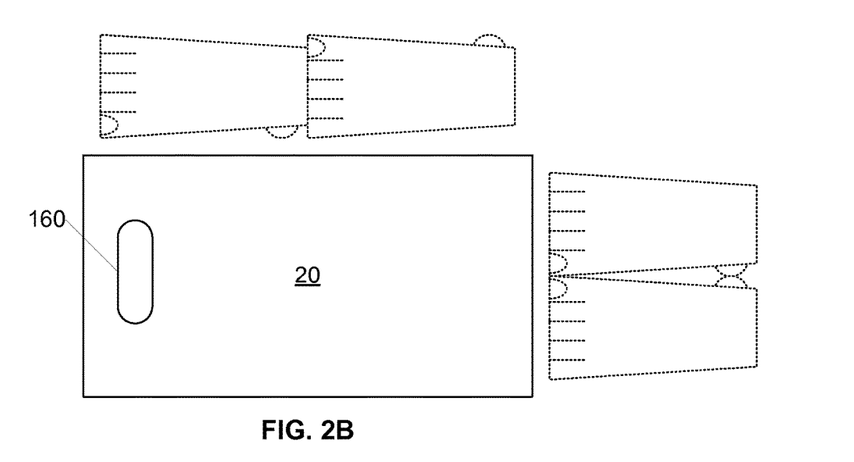
FIG. 2B is a block diagram illustrating a top view of an example balance board according to an embodiment of the invention.

FIG. 2B is a block diagram illustrating a top view of an example balance board 20 according to an embodiment of the invention. In the illustrated embodiment, the balance board 20 comprises an opening 160 that is cut out from the interior of the balance board 20 and functions as a handle. Alternatively, the balance board 20 may include a handle (not shown) that extends from an edge or the top or bottom surface of the balance board 20, for example, from the bottom surface. Advantageously, the length of the balance board 20 is sized to accommodate large feet situated heel-to-toe and the width of the balance board 20 is sized to accommodate large feet situated ankle-to-ankle. In an alternative embodiment, the width of the balance board 20 is sized to accommodate large feet situated ankle-to-ankle and the diagonal of the balance board 20 is sized to accommodate large feet situated heel-to-toe. Such an embodiment advantageously reduces the surface area of the balance board 20 to make the balance board 20 more compact, light and portable.

In one embodiment, the balance board 20 is rectangular and comprises a top surface and a bottom surface and four side edges. Also in this embodiment, there are four feet and each of the four feet each include a proximal surface that faces the bottom surface of the balance board 20 and a distal surface that faces away from the bottom surface of the balance board 20. Each foot may have one or more side edges (e.g., one side edge for a circular shape, three side edges for a triangular shape, four side edges for a rectangular shape, etc.). Each of the four feet engage (e.g., are affixed to) the bottom surface of the balance board 20 and one foot is placed in each of the four corners. In this embodiment, the feet are placed in the corners so that the side edge(s) of the feet closest to two side edges of the balance board 20 are equidistant from those two side edges of the balance board 20. Also in this embodiment, the feet are independently adjustable to account for an uneven surface. The independently adjustable feet allow the balance board 20 to be placed on the ground and adjusted so that the top surface of the balance board 20 is level. Accordingly, the distance from the distal surface of each foot to the bottom surface of the balance board 20 is independently adjustable.

Figure 3:
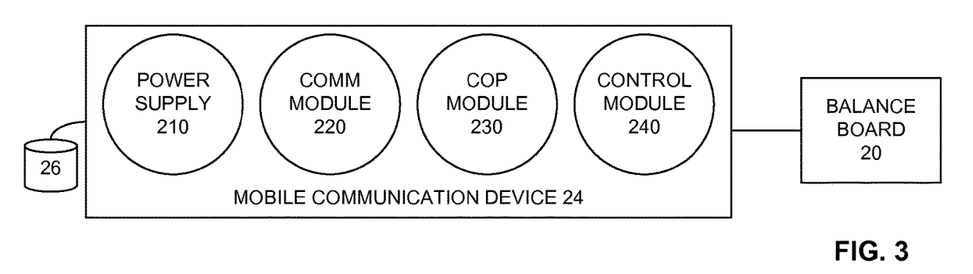
FIG. 3 is a block diagram illustrating an example mobile communication device according to an embodiment of the invention.

FIG. 3 is a block diagram illustrating an example mobile communication device 24 according to an embodiment of the invention. The mobile communication device 24 is a processor enabled device as previously discussed and may be a laptop computer, a smartphone, a personal digital assistant, just to name a few example processor enabled devices. In the illustrated embodiment, the device 24 comprises a power supply 210, a communication module 220, a COP module 230 and a control module 240. Additional modules may also be included.

The power supply module 210 is configured to regulate and provide power to the device 24, for example from an internal power source such as a battery or an external power source such as a power outlet.

The communication module 220 is configured to communicate with a balance board to receive sensor data from the balance board. Such communication may be implemented using a wireless link or a wired link. In alternative embodiments, the communication module 220 may in fact be a USB cable, a SMART module or an IrDA module, or the like—depending on the communication protocol employed by the device 24 and the balance board 20. The communication module 220 may receive raw sensor data (COP data) or it may also receive path length data if the balance board 20 (e.g., the circuit board or other hardware or software modules) is configured to perform calculations on the COP data from the plurality of sensors on the balance board 20 and generate path data.

The COP module 230 is configured to receive the raw sensor data from a balance board 20 and calculate the COP over time. In one embodiment, the COP module 230 calculates COP using the following formulas, where the balance board 20 has four feet and TR, TL, BR and BL are the sensor values from the top right, top left, bottom right and bottom left sensors, respectively:

$$COPx = (\text{platform length})/2 * ((TR+BR)-(TL+BL))/(TL+TR+BL+BR)$$

$$COPy = (\text{platform width})/2 * ((TL+TR)-(BL+BR))/(TL+TR+BL+BR)$$

The control module 240 is configured to use the COP data from the COP module 230 and calculate a path length value for the subject using the following formula, where COPx2 and COPx1 are adjacent time points in the COPx time series and COPy2 and COPy1 are adjacent time points in the COPy time series:

$$\text{Path Length} = ((COPx2-COPx1)^2 + (COPy2-COPy1)^2)^{0.5}$$

The path length value is one representation of how much the subject swayed during the time period of a single balance test (e.g., one balance test in the battery of balance tests included in BESS) in both the X and Y directions. As will be understood by those skilled in the art, alternative COP size measurements other than path length may be employed, for example, the maximum distance in the fore-aft or medial-lateral directions.

Figure 4A:
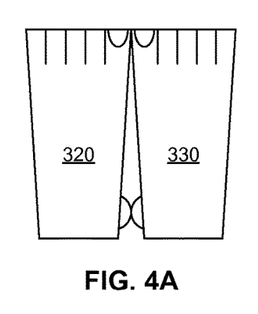
FIGS. 4A-4C are block diagrams illustrating an example series of subject positions for the BESS test according to an embodiment of the invention.
Figure 4B:
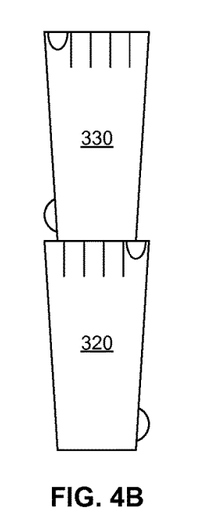
Figure 4C:
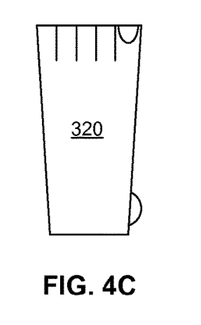

FIGS. 4A-4C are block diagrams illustrating an example series of subject positions for the BESS test according to an embodiment of the invention. In FIG. 4A, the subject is standing ankle to ankle with the left foot 320 next to the right foot 330 on top of the platform of the balance board. In FIG. 4B, the subject is standing heel-to-toe with the right foot 330 in front of the left foot 320. In FIG. 4C, the subject is standing with one foot on the balance board.

In one embodiment, during the BESS test the subject rotates 90 degrees on the platform of the balance board when transitioning from the one foot balance test or the ankles together balance test to the heel-to-toe balance test, or vice versa. Advantageously, the dimensions of the platform are selected such that the feet of the subject fit entirely on the board during each balance test in the BESS battery.

Figure 5:
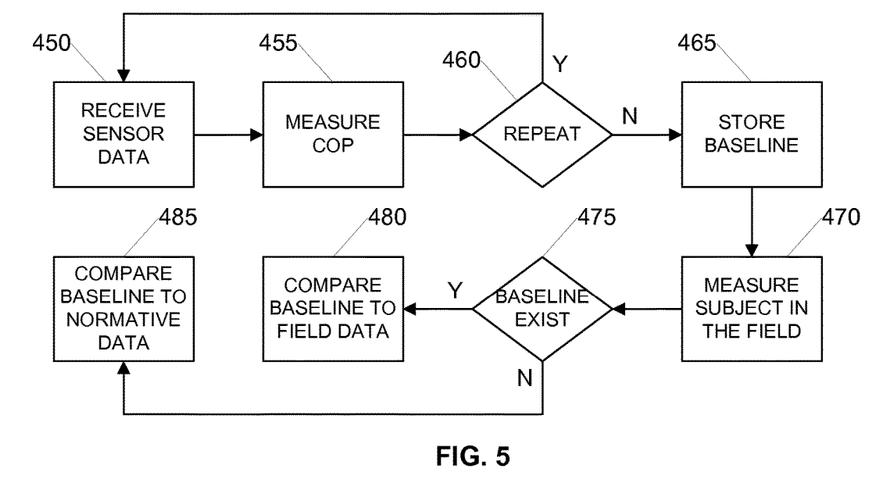
FIG. 5 is a flow diagram illustrating an example process for detecting clinically relevant changes in balance of a person according to an embodiment of the invention.

FIG. 5 is a flow diagram illustrating an example process for detecting clinically relevant changes in balance of a person according to an embodiment of the invention. The illustrated process can be implemented by the system previously described in FIGS. 1-3. Initially, in step 450 first sensor data is received from the sensors in the feet of the balance board. The sensor data is analyzed to measure a first COP as shown in step 455. If sufficient COP data has not yet been measured (or alternatively if the subject has not been standing on the balance board for sufficient time), as determined in step 460, the process loops back and receives second (and so on) sensor data and analyzes the second (and so on) sensor data to measure a second (and so on) COP. Once sufficient COP data has been measured, as determined in step 460, a baseline path length is stored in step 465 and associated with an identifier for the subject.

Later, in the field and after the baseline path length has been stored in step 465, the subject is evaluated on a balance board (not necessarily the same balance board) and a field path length is determined in step 470. Next, if a baseline path length has been stored for the particular subject as determined in step 475, the field path length is compared to the baseline path length in step 480 to determine whether or not a clinically relevant change in balance is present for the subject. Alternatively, if a baseline path length has not been stored for the particular subject as determined in step 475, the field path length is compared to a normative path length in step 485 to determine whether or not a clinically relevant change in balance is present for the subject. The normative path length can be predetermined and stored and associated with a variety of individual subject characteristics. The specific subject's individual characteristics can then be matched to the normative characteristics to allow a given subject's baseline to be approximated and compared to the field path length.

Clinically relevant changes in balance can be symptomatic for concussions, stroke, Parkinson's disease, multiple sclerosis, cerebral palsy and any other neuromuscular disease and/or disability condition. Advantageously, the system can objectively detect clinically relevant changes in balance and can therefore be used as an objective diagnostic tool for a variety of neuromuscular diseases and/or disability conditions.

In one embodiment, the method in FIG. 5 employs balance conditions associated with the BESS test to establish the baseline path length. This baseline path length can then be used to facilitate diagnosis of a concussion in the field. In an alternative embodiment, the baseline path length can be established using balance conditions associated with the Romberg test.

Comparative Example

A study was conducted by the inventor to quantify the validity and reliability of a Portable small form factor COP tracking device for objectively scoring the BESS balance protocol. Body sway data were collected concurrently from a scientific grade force plate and a balance board, as healthy young adults performed the BESS test on each of two days separated by one week. Balance trials were also videotaped and observationally scored by three trained raters.

Participants

Thirty young adults (mean age=24.4±3.9 years; 15 men, 15 women) participated in this study. This sample size was deemed adequate for ensuring the stability and precision of the reliability and validity coefficients calculated in the context of this study. Subjects were in good general health according to the Physical Activity Readiness Questionnaire. In addition, subjects were concussion-free based on the Standard Assessment of Concussions checklist and the Concussions Symptoms checklist. Several testing conditions required knowledge of participant's dominant leg. Footedness was, therefore, determined by asking participants which leg they preferred for kicking a ball. As expected, the majority of subjects were right footed.

Experimental Setup

Figure 6:
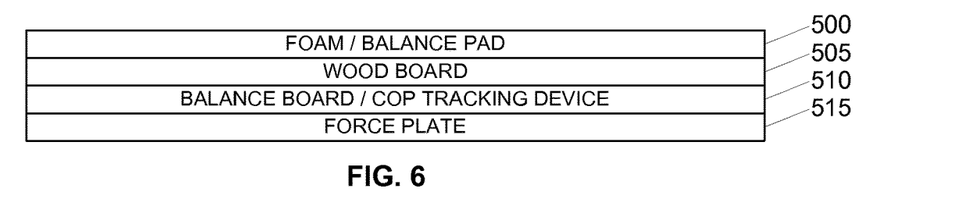
FIG. 6 is a block diagram illustrating a side view of an example comparative balance board apparatus used in the comparative example described herein.

A schematic of the experimental setup for this study is shown in FIG. 6. For each balance trial conducted (see experimental procedures), participants stood on top of a portable small form factor COP tracking device 510 ("balance board") that was affixed to the top of a scientific grade force plate 515 (model: OR6-7-2000, Advanced Mechanical Technology, Inc., Watertown, Mass., USA) with industrial strength Velcro. Mechanically-coupled to the balance board was a firm wood board 505 sized to accommodate large feet and the tandem stance balance conditions. In some trials, a removable balance pad 500 (Alcan Airex, Aargau, CH) was placed on the wood board 505 to provide an unstable surface for standing.

Body sway data in the side to side (COPx) and fore-aft (COPy) directions were recorded from the force plate 515 and balance board 510 by a personal computer (not shown, e.g., Dell Optiplex 990, Dell Inc., Round Rock, Tex., USA) via a customized data collection program written in LabVIEW (National Instruments, TX, USA). The force plate 515 signals were amplified by a mini-amp (not shown, e.g., model: MSA-6, Advanced Mechanical Technology, Inc., Watertown, Mass.) and brought into the computer via a 64 channel analogue data acquisition board (not shown, e.g., model: USB-2533, Measurement Computing, MA, USA). Alternatively, the balance board 510 was connected wirelessly to the personal computer via Bluetooth technology. All data trials were additionally recorded with a web camera (not shown, e.g., model: Quickcam Pro 5000, Logitech, Calif., USA), using commercially available video capturing software (Camerasoft Webcam Recorder v.3.1.08, Camerasoft Studio, USA).

Experimental Procedures

Following the health screening described previously, participants began the balance testing portion of the study by changing into appropriate clothing and removing all footwear. A short familiarization period was then given to allow participants time to experience the following stance and surface conditions of the BESS protocol:

Condition 1—Double leg stance on a firm (wood board 505) surface

Condition 2—Single leg stance on a firm (wood board 505) surface

Condition 3—Tandem stance on a firm (wood board 505) surface

Condition 4—Double leg stance on an unstable (foam 500) surface

Condition 5—Single leg stance on an unstable (foam 500) surface

Condition 6—Tandem stance on an unstable (foam 500) surface

In each condition, the participant was instructed to keep his/her hands on the hips and eyes closed. Double leg stance conditions required the participant to keep both feet on the surface with medial sides in contact. Single leg stance involved standing on the non-dominant leg while lifting the foot of the dominant leg off the surface to an angle that was approximately 45 degrees of knee flexion and 30 degrees of hip flexion. Lastly, tandem stance was a condition where participants placed their feet heel to toe.

Once familiar with the balance conditions, testing began in earnest. Test instructions were standardized and read as prompted from the data collection computer screen. Each participant performed the balance conditions one at a time and in the same order as listed above. Participants were told to remain as still as possible while maintaining the desired test position, and to only open their eyes to reposition themselves following a loss of balance. Each trial lasted 20 seconds and began when the desired test position was held stable for several seconds with eyes closed. The total test time was less than 5 min, and repeat testing occurred seven days after the initial data collection at a similar time of day.

Data Processing

Force Plate 515 and Balance Board 510 COP Determination

COP was calculated for the force plate 515 using the following formulas:

$$COPx = My/Fz$$

$$COPy = Mx/Fz$$

Where My and Mx were the moments of force generated about the y and x axes of the force plate 515 respectively, and Fz was the total downward (i.e. vertical) force.

For the balance board 510, more simplistic COP calculations were utilized due to the fact that the balance board 510 does not measure moments of force. In this case, the following formulas were utilized:

$$COPx = (\text{platform length})/2*((TR+BR)-(TL+BL))/(TL+TR+BL+BR)$$

$$COPy = (\text{platform width})/2*((TL+TR)-(BL+BR))/(TL+TR+BL+BR)$$

Where TR, TL, BR and BL are the force sensor values from the top right, top left, bottom right and bottom left corners of the balance board 510.

Some participants stepped off of the balance board 510/force plate 515 during testing, particularly in the more difficult single leg and tandem stance on foam 500 conditions. In this case, an algorithm was utilized that pushed COPx and COPy 100 cm from the center location of the balance board 510 when the concurrently recorded weight for the participant fell below a reading of 20 Kg. This penalty was determined based on an approximation of the amount of COP displacement that would occur during a typical fall. When the participant returned to standing on the balance board 510/force plate 515, the COP measurement returned to normal.

For each BESS condition and for the sum of all conditions (i.e. composite score) the balance board 510 and force plate 515 COP data were used to calculate a total COP path length value. This nondimensional, point to point measure of the total movement of the COP trace was used as the main outcome measure describing body sway during the balance testing. This variable was calculated according to the following formula:

$$\text{Path Length} = ((COPx2-COPx1)^2 + (COPy2-COPy1)2)^{0.5}$$

Where COPx2 and COPx1 are adjacent time points in the COPx time series and COPy2 and COPy1 are adjacent time points in the COPy time series. In this way, the sum of all points was added together to get total path length.

Observation-Based (i.e. Rater-Determined) BESS Scores

From the videos taken of each trial with the webcam, three trained raters scored the balance performance of all participants according to the clinical BESS guidelines. In this case, an error count was established in a single viewing of the videos for each condition and for the overall (i.e. composite) score. The following errors were noted:
1. Moving the hands off of the hips
2. Opening of the eyes
3. Step, stumble or fall
4. Abduction or flexion of the hip beyond 30 degrees
5. Lifting the forefoot or heel off the testing surface
6. Remaining out of the test position for >5 seconds The three raters in this study had varying levels of experience with the BESS, with one rater having extensive experience (>3 years, frequency of use ~2-3 times a month), one intermediate (>2 years, frequency of use ~once a month) and one being a novice (<1 year, no BESS use outside of this study). The two more experienced raters were trained in the BESS as a part of their university athletic training curriculum, while the novice was recently trained on the BESS and allowed to practice for 2 weeks prior to data collection.

Statistical Analyses

Concurrent Validity of Balance Board 510 and BESS Scores Versus the Force Plate 515

Concurrent validity was examined for the both the balance board 510 and observation-based BESS compared to the force plate 515 using Pearson Product Moment Correlations in each of the six BESS conditions, and for composite scores. While Bland-Altman plots and repeated measures analyses are sometimes used in conjunction with correlations to examine validity, the balance board 510 and force plate 515 COP calculations differ (based on moment of force measurement as described above), precluding these analyses. Validity coefficients ≥±0.90 were considered excellent, between 0.80 and 0.89 good, between 0.70 and 0.79, fair, and values below 0.70 were considered poor evidence of concurrent validity.

Reliability for the Observation-Based BESS Scores, Force Plate 515 and Balance Board 510

Inter-rater reliability for the observation-based BESS was examined for the three raters using an ICC two-way random effects, single measure model, as the three raters were considered a representative sample from a larger population of raters who would normally use the BESS. Seven day test-retest reliability for the scientific grade force plate 515, balance board 510, and observation-based BESS balance tests were examined using an ICC model. Reliability coefficients (R)≥0.75 were deemed excellent, between 0.60 and 0.74 good, between 0.40 and 0.59 fair, and below 0.40 poor.

Results

General Observations

Figure 7:
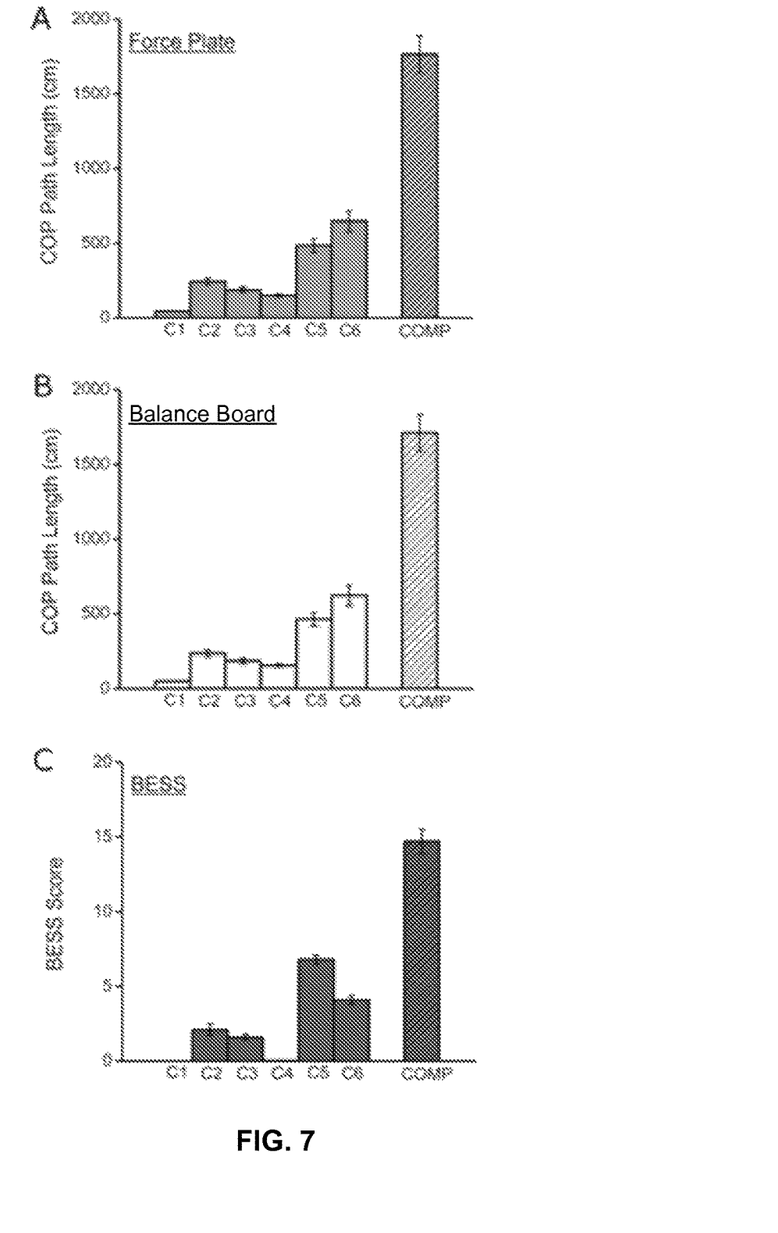
FIGS. 7-9 are graph diagrams illustrating comparative balance test performance data from the comparative example described herein.
Figure 8:
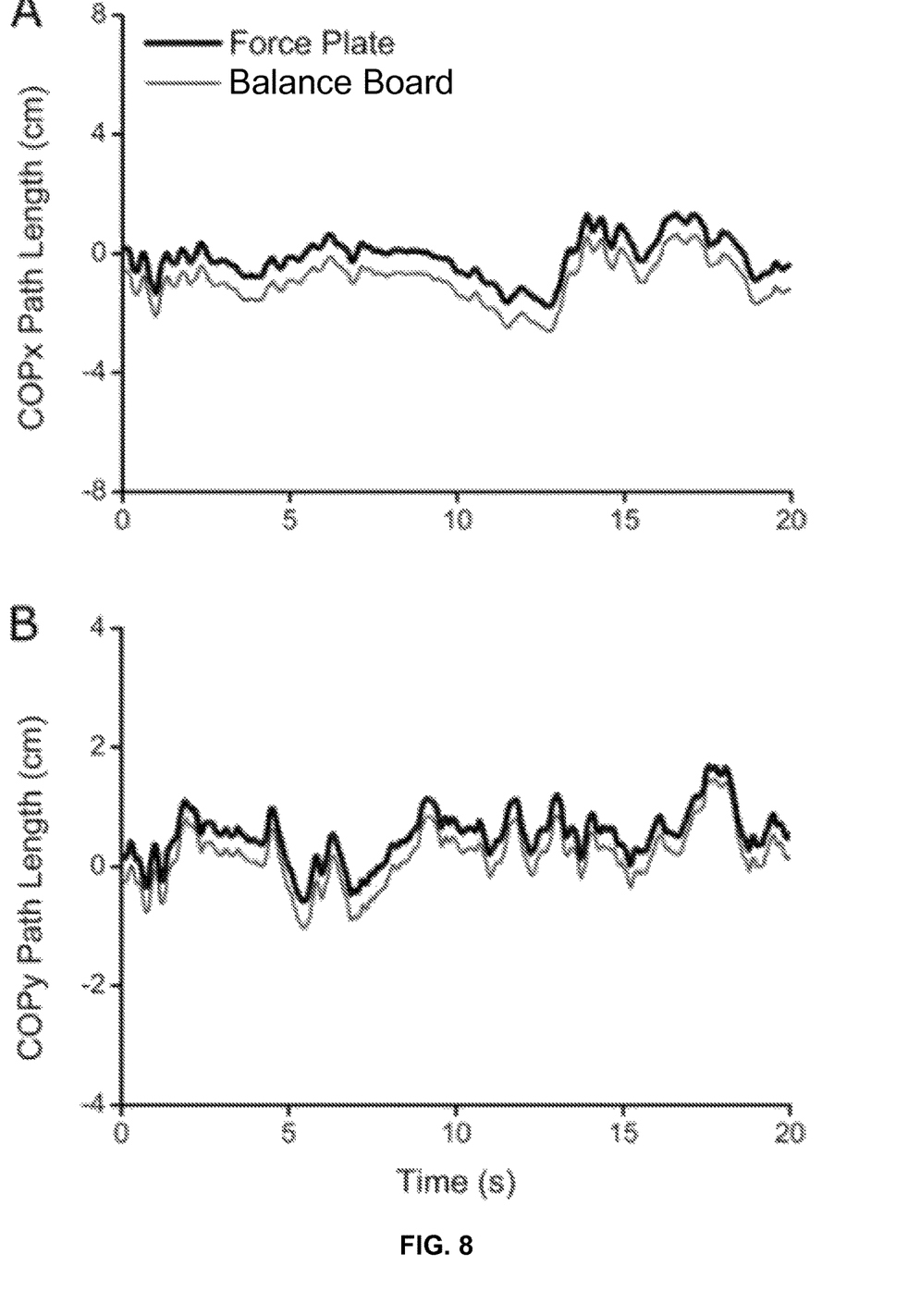

All participants completed the full test-retest protocol with no reported incidents or discomfort. The mean (±standard error) test performance for each balance condition, and composite score, is provided in FIG. 7 for the force plate 515, balance board 510 and observation-based BESS scores. Overall, the low cost balance board 510 utilized in the present study provided excellent within trial agreement with the expensive, gold standard force plate 515. Examples of raw COPx (i.e. Side to side) and COPy (i.e. Fore-Aft) data are provided in FIG. 8. These typical results show that the two devices generated body sway data that was very similar. This high degree of correspondence was evident regardless of the subject (male/female, short/tall) or balance condition (condition 1-6) tested. The balance board 510 was equally, highly related to the force plate 515 on both the first and second balance tests conducted.

Validity

Comparisons between the scientific grade force plate 515, balance board 510 and rater-determined BESS scores are summarized in Table 1 below.

TABLE 1

Validity measures (r-values) for the balance board 510 and BESS raters versus the force plate 515.

| Scoring Category | Balance Board vs. Force Plate | | BESS Score vs. Force Plate | |
|---|---|---|---|---|
| | Test | Retest | Test | Retest |
| Condition 1 | 0.99 | 0.99 | — | — |
| Condition 2 | 0.99 | 0.99 | 0.31-0.60 | 0.57-0.70 |
| Condition 3 | 0.99 | 0.99 | 0.25-0.55 | 0.29-0.38 |
| Condition 4 | 0.99 | 0.99 | 0.16-0.40 | 0.17-0.29 |
| Condition 5 | 0.99 | 0.99 | 0.08-0.21 | −0.04-0.13 |
| Condition 6 | 0.99 | 0.99 | 0.23-0.42 | −0.01-0.63 |
| Composite | 0.99 | 0.99 | 0.21-0.52 | 0.10-0.47 |

Figure 9:
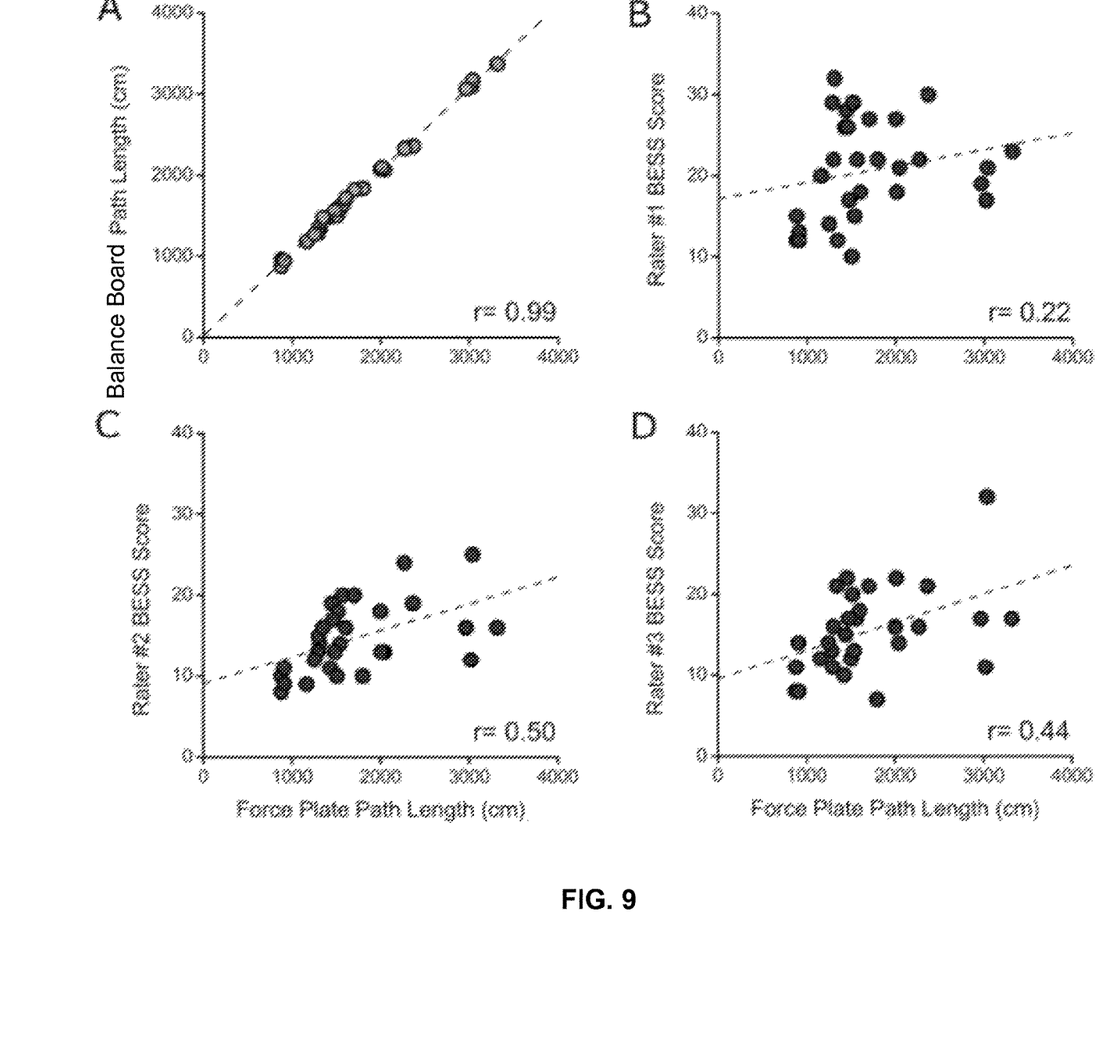

Not surprisingly, based on their within trial correspondence, the balance board 510 showed a near perfect (r=0.99) correlation with the gold standard force plate 515 in each balance test condition and for the composite COP path length calculated. This accuracy level was achieved despite the use of a more simplistic means of quantifying center of pressure that did not require determination of moments of force. In contrast, the observational BESS scores determined by the three raters varied substantially across balance conditions and raters. In condition 1, validity could not be established, based on the lack of any errors noted by any rater. For the remaining conditions (Conditions 2-6), correlations between the rater-determined BESS scores and the force plate 515 data ranged from only from low to fair (Test r=0.08-0.60; Retest r=−0.04-0.70) in strength. Composite BESS scores were low (Test r=0.21-0.52; Retest r=0.10-0.47) in all cases, providing little evidence for concurrent validity. These findings are demonstrated further in FIG. 9, which compares the composite data for the balance board 510 and each rater relative to the force plate 515.

Inter-Rater Reliability

Contributing to the poor validity of the rater-determined BESS scores relative to balance board 510 was a less than optimal amount of inter-rater reliability (see Table 2 below).

TABLE 2

Inter-rater reliability (ICCs) between the three trained BESS raters.

| Scoring Category | Test | Retest |
|---|---|---|
| Condition 1 | — | — |
| Condition 2 | 0.60 | 0.69 |
| Condition 3 | 0.47 | 0.33 |
| Condition 4 | 0.24 | 0.00 |
| Condition 5 | 0.46 | 0.37 |
| Condition 6 | 0.35 | 0.20 |
| Composite | 0.35 | 0.20 |

ICCs were poor to good ranging from R=0.24-0.60 at time point one (i.e. test), and R=0.00-0.69 at time point two (i.e. retest). Inter-rater reliability was particularly poor in Conditions 4 and 6, as well as for the composite scores obtained by the three raters. These results suggest that subjectivity and/or human error impacted the observation-based BESS scores.

Test-Retest Reliability

The high degree of agreement between the balance board 510 and gold standard force plate 515 shown above clearly demonstrates that balance board 510 data are accurate. However, of equal importance for the management of sports-related concussion is the test-retest reliability of this device. This is due to the fact that most concussion protocols call for repeated testing of balance ability on multiple days in order to track changes in balance performance relative to a previously determined baseline value.

Test-retest reliability of the force plate 515, balance board 510 and BESS scores calculated in the present study are summarized in Table 3 below.

TABLE 3

Test-retest reliabilities (ICCs) for the force plate 515, balance board 510 and BESS raters.

| Scoring Category | Force Plate | Balance Board | BESS raters |
|---|---|---|---|
| Condition 1 | 0.66 | 0.68 | — |
| Condition 2 | 0.65 | 0.59 | 0.56-0.73 |
| Condition 3 | 0.28 | 0.27 | 0.38-0.57 |
| Condition 4 | 0.75 | 0.73 | 0.00-0.38 |
| Condition 5 | 0.55 | 0.51 | 0.23-0.63 |
| Condition 6 | 0.71 | 0.71 | 0.33-0.51 |
| Composite | 0.89 | 0.88 | 0.61-0.78 |

Despite having poor test-retest reliability in Condition 3, the force plate 515 and balance board 510 had moderate to good test-retest reliability for all other conditions. In addition, and most importantly, the balance board 510 and force plate 515 both showed excellent (balance board 510 R=0.88; force plate 515 R=0.89) test-retest reliability in the composite COP path length determined. This value was greater than that found for the composite BESS scores determined by any of the individual raters (R=0.61-0.78). ICCs for the rater determined scores in condition 1 were not possible due to a lack of variability in the data (i.e. all raters scored this condition zero errors for all participants). The lowest reliability for rater-determined BESS scores was in Condition 4 (R=0.00-0.38) and the highest was in Condition 2 (R=0.56-0.73).

Discussion

The goal of the present study was to determine whether a low cost balance board 510 that does not measure moments of force could be utilized for improving the validity/reliability of a recommended balance test in the realm of sports-related concussion (i.e. the BESS). Compared to measuring body sway during balance tasks performed while standing on a sophisticated scientific grade force plate 515, the inexpensive balance board 510 proved to be superior to the observational BESS scores determined by three raters. Specifically, the low cost balance board 510, which uses an alternative means of calculating COP, had an almost perfect agreement with force plate 515 data in terms of COP measured during all trails conducted. This level of validity was notably higher than any rater-determined BESS score, regardless of experience level. In addition, the test-retest reliability of the balance board 510 composite scores was consistently very high, whereas observation-based BESS scores ranged from only fair to excellent. Taken together, these results suggest that a low cost COP tracking device such as the balance board 510 may provide an improved means for conducting balance assessments in the realm of sports-related concussion.

The concurrent validity of observational BESS scores relative to a force plate 515 was initially determined in a seminal study by Riemann. In this study, 111 athletes were rated by three experienced athletic trainers using observation-based BESS criteria while COP data was concurrently recorded from a Neurocom balance master longboard. Similar to the results of the present study, correlations between the BESS scores and force plate 515 COP covered a wide range (r=0.31-0.79) across the various conditions, with no correlation possible in Condition 1 (double stance on firm) due to a lack of errors perceived. In contrast, the low cost balance board 510 used in the present study had excellent concurrent validity (r=0.99) in all conditions and provided meaningful Condition 1 data for comparison.

In terms of reliability, the present study showed greater performance for the balance board 510 versus observation-based BESS scores in each condition and in terms of composite score. Test-retest reliability for the observational BESS method has previously been reported to be good for high school participants (ICC=0.70) (27) and young adults (Generalizability Coefficient 0.64) (3). The present findings agree with this work, finding ICC values of 0.61-0.78 for the composite scores of a group of healthy young adults. Despite these overall positive findings, the low cost balance board 510 in the present study was able to further improve test-retest reliability of the BESS, with the noted advantage of eliminating issues of poor inter and intra-rater reliability. With respect to the later factor, intra-rater reliability has been shown to range from 0.6 to 0.92 on the total BESS score, indicating the BESS, while quantitative, is prone to some degree of subjectivity in its determination.

Perhaps the greatest strength of a low cost COP measurement device for scoring the BESS is improvement in inter-rater reliability. For any given BESS test conducted using the balance board 510, similar scores should be generated regardless of the operator. This is in stark contrast to observation-based BESS scores, which are known to vary significantly between raters scoring the same trials. This was demonstrated in the present study as well, where three trained raters obtained BESS scores that varied substantively for the various conditions and, importantly, for the composite BESS score. Given the issue of inter-individual consistency, it would seem necessary that all BESS scores done observationally should be obtained by the same rater to ensure reliability. Unfortunately, this approach is not always feasible in settings with multiple athletic trainers whose patient care may overlap. Balance assessment using a device like the balance board 510, would allow different athletic trainers with multiple levels of experience to score the BESS at different time points and still ensure that the numbers generated are comparable in practice.

Previous studies utilizing a force plate 515 have shown that balance testing has the necessary specificity and sensitivity to diagnose concussion related postural disturbances. Given the agreement shown in the present study between a force plate 515 that does measure moments of force and the low cost balance board 510 that does not measure moments of force, it seems likely that a balance board 510 could provide the same level of athlete-related diagnostic information to sports medicine professionals. To this extent, while it is understood that a larger COP path length represents a decline in overall balance ability relative to a baseline testing session, there are no standard criteria for how much greater this value must be to indicate a concussion. Future work aimed at determining this criterion from a large database of normative values will be necessary to assist sports clinicians in making such determinations from this now feasible balance board 510 system.

Summary and Conclusions

In the present study it was shown by the inventor that an inexpensive COP tracking device (i.e. balance board 510) could be utilized to improve the validity/reliability of BESS balance tests that are currently scored visually by sports medicine professionals. This device, even with the need to utilize a personal computer or laptop to run collection software, provides an more affordable (<$1000 US) solution that merges high tech and low tech balance testing approaches, which currently subsist in isolation. Utilizing this "mid-tech" approach in the future could provide a new standard of care for sports-related concussion testing.

Example Computing Device

Figure 10:
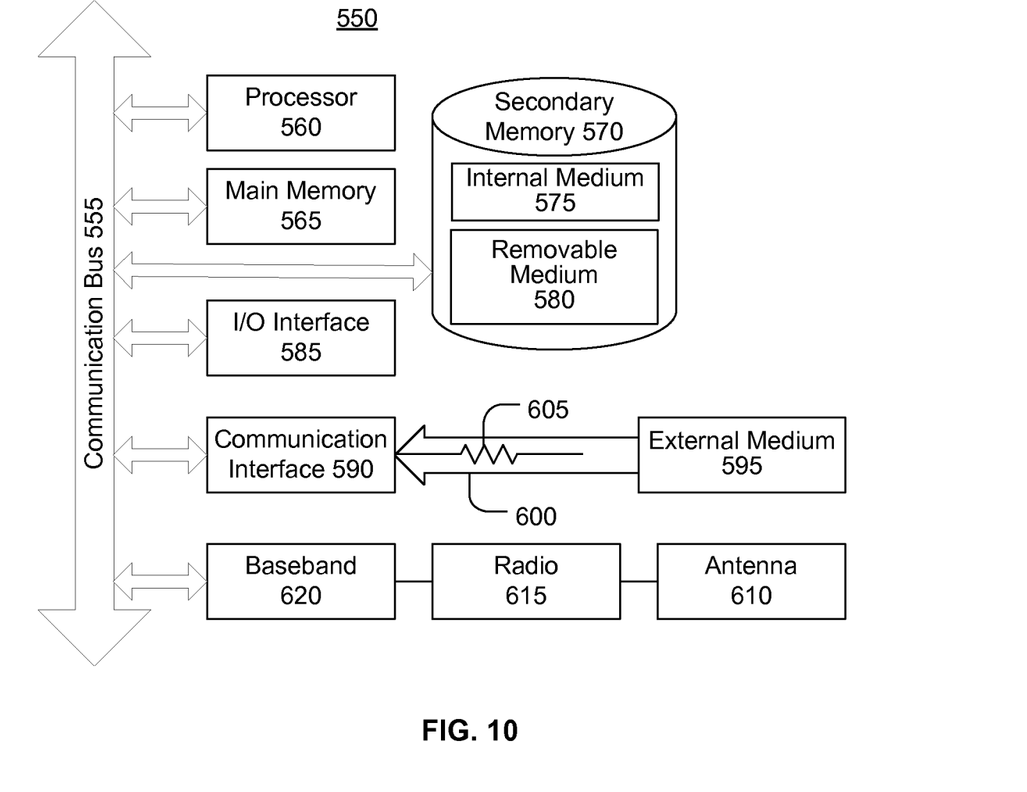
FIG. 10 is a block diagram illustrating an example wired or wireless processor enabled device that may be used in connection with various embodiments described herein.

FIG. 10 is a block diagram illustrating an example wired or wireless system 550 that may be used in connection with various embodiments described herein. For example the system 550 may be used as or in conjunction with a balance board, mobile communication device, or server as previously described with respect to FIGS. 1-3. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615. In alternative embodiments, the RF signals may include Bluetooth and/or Zigbee and/or other wireless communication protocols.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter that is broadly contemplated by the present invention. It is further understood that the scope of the present invention fully encompasses other embodiments that may become obvious to those skilled in the art and that the scope of the present invention is accordingly not limited.

What is claimed is:

1. A technical system for detecting clinically relevant changes in balance, the system comprising:
   (i) a portable balance board, and (ii) a processor-enabled companion device connected to the portable balance board;
   wherein the portable balance board is 20-24" in length and 14-15" in width to accommodate both ankle-to-ankle and heel-to-toe standing positions of Balance Error Scoring System (BESS) testing, and wherein the portable balance board is supported by at least four (4) feet, each of said four feet are adjustable in height, and each of said feet has an integrated downward-force sensor communicating downward-force sensor data to the companion device, wherein the balance board does not measure moments of force;
   at least one non-transitory computer readable medium in the companion device configured to store executable programmed modules;
   at least one processor in the companion device communicatively coupled with the non-transitory computer readable medium configured to execute programmed modules stored therein;
   a control module stored in the at least one non-transitory computer readable medium and configured to be executed by the processor, the control module configured to receive downward force sensor data from the integrated downward-force sensors and calculate center of pressure (COP) over time data, the control module further configured to calculate a field path length for a first subject based on the center of pressure (COP) over time data, the control module further configured to compare the field path length for the first subject to a predetermined baseline path length for the first subject obtained from the non-transitory computer readable medium;
   further comprising a center of pressure (COP) module stored in the at least one non-transitory computer readable medium and configured to be executed by the processor, the center of pressure (COP) module configured to receive the downward force sensor data and calculate a center of pressure (COP) value for each of a plurality of time increments and provide said center of pressure values for each of said plurality of time increments to the control module;

wherein the downward force sensor data comprises a downward force sensor data value from each integrated sensor in each of said feet;

wherein the center of pressure value is calculated using the following equations:

$$COPx = (\text{platform length})/12 * (TR+BR) - (TL+BL))/(TL+TR+BL+BR)$$

$$COPy = (\text{platform width})/2 * ((TL+TR) - (BL+BR))/(TL+TR+BL+BR)$$

wherein TR, TL, BR and BL are downward force sensor data values from a top right (TR), a top left (TL, a bottom right (BR) and a bottom left (BL) integrated downward-sensor in said feet; and, wherein the field path length is calculated using the following equation:

$$\text{field path length} = ((COPx2-COPx1)^2 + (COPy2-COPy1)^2)^{0.5}$$

wherein said field path length calculation provides a r=0.99 correlation when compared to an output of a Gold Standard force plate.

* * * * *